(12) United States Patent
Jeong et al.

(10) Patent No.: US 11,305,239 B2
(45) Date of Patent: Apr. 19, 2022

(54) PERMEABLE MEMBRANE SUPPORT WITH A DETACHABLE PERMEABLE MEMBRANE

(71) Applicant: ST1 CO., LTD., Busan (KR)

(72) Inventors: Young Hun Jeong, Daegu (KR); Yong Jun Yoon, Busan (KR)

(73) Assignee: ST1 CO., LTD., Busan (KR)

( * ) Notice: Subject to any disclaimer, the term of this patent is extended or adjusted under 35 U.S.C. 154(b) by 0 days.

(21) Appl. No.: 16/864,737

(22) Filed: May 1, 2020

(65) Prior Publication Data
US 2021/0346850 A1 Nov. 11, 2021

(30) Foreign Application Priority Data

Jan. 30, 2020 (KR) .................. 10-2020-0010770

(51) Int. Cl.
| | | |
|---|---|---|
| *B01D 69/10* | (2006.01) | |
| *B01D 63/08* | (2006.01) | |
| *B01D 65/00* | (2006.01) | |
| *B01D 69/06* | (2006.01) | |

(52) U.S. Cl.
CPC ........... *B01D 69/10* (2013.01); *B01D 63/087* (2013.01); *B01D 65/003* (2013.01); *B01D 69/06* (2013.01); *B01D 2313/04* (2013.01); *B01D 2313/06* (2013.01); *B01D 2313/20* (2013.01)

(58) Field of Classification Search
CPC ...... B01D 69/10; B01D 69/06; B01D 63/087; B01D 65/003; B01D 2313/20; B01D 2313/06; B01D 2313/04
See application file for complete search history.

(56) References Cited

U.S. PATENT DOCUMENTS

| | | | | |
|---|---|---|---|---|
| 4,301,010 A * | 11/1981 | Eddleman | ............ | B01D 29/085 |
| | | | | 210/406 |
| 5,308,483 A * | 5/1994 | Sklar | .................... | B01D 29/085 |
| | | | | 210/232 |
| 5,603,900 A * | 2/1997 | Clark | .................. | B01D 29/012 |
| | | | | 422/535 |
| 8,808,552 B2 * | 8/2014 | Lin | ...................... | B01D 29/085 |
| | | | | 210/808 |
| 9,267,101 B2 * | 2/2016 | Schmidt | .................... | A61P 3/10 |
| 2003/0106609 A1 * | 6/2003 | Leoncavallo | ........... | B67C 11/02 |
| | | | | 141/340 |
| 2003/0213740 A1 * | 11/2003 | Creasey | ................. | B01D 61/28 |
| | | | | 210/321.6 |

(Continued)

FOREIGN PATENT DOCUMENTS

| | | |
|---|---|---|
| JP | 2007-167002 | 7/2007 |
| KR | 10-1900466 | 9/2018 |

*Primary Examiner* — Krishnan S Menon
(74) *Attorney, Agent, or Firm* — Norton Rose Fulbright US LLP

(57) ABSTRACT

Disclosed is a permeable membrane support having an attachable and detachable permeable membrane, the permeable membrane support comprising: a lower support; an upper support partially accommodated into the lower support; and a permeable membrane disposed between the lower support and the upper support. When the upper support and the lower support are engaged with each other in a snap-fit manner, the permeable membrane is sandwiched between a bottom opening of a cylindrical lower member of the upper support and a top face of a bottom support portion of the lower support.

8 Claims, 12 Drawing Sheets

(56) References Cited

U.S. PATENT DOCUMENTS

| | | | |
|---|---|---|---|
| 2007/0062870 A1* | 3/2007 | Chen | B01D 61/147 |
| | | | 210/636 |
| 2011/0313143 A1* | 12/2011 | Martin | B01L 3/50255 |
| | | | 536/23.1 |
| 2014/0322743 A1* | 10/2014 | Tang | G01N 1/4005 |
| | | | 435/29 |
| 2015/0185184 A1* | 7/2015 | Guia | B01D 57/02 |
| | | | 204/543 |

* cited by examiner

【FIG. 1】
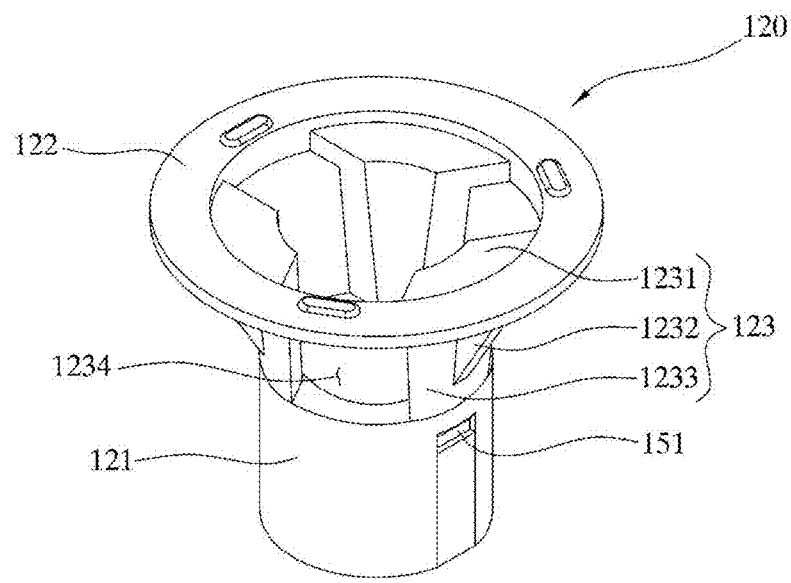
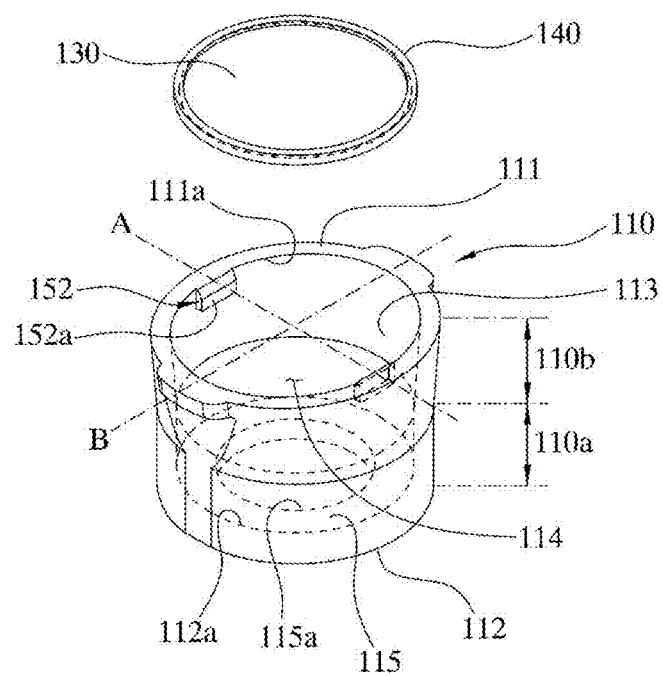

[FIG. 2]
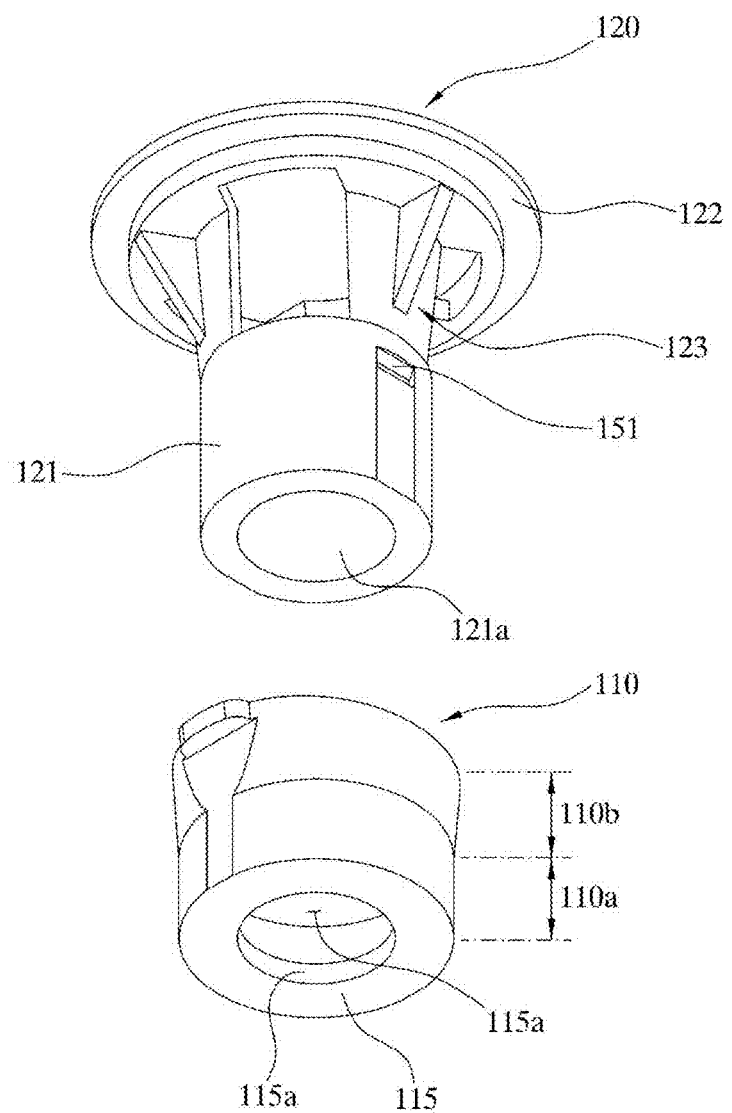

【FIG. 3】
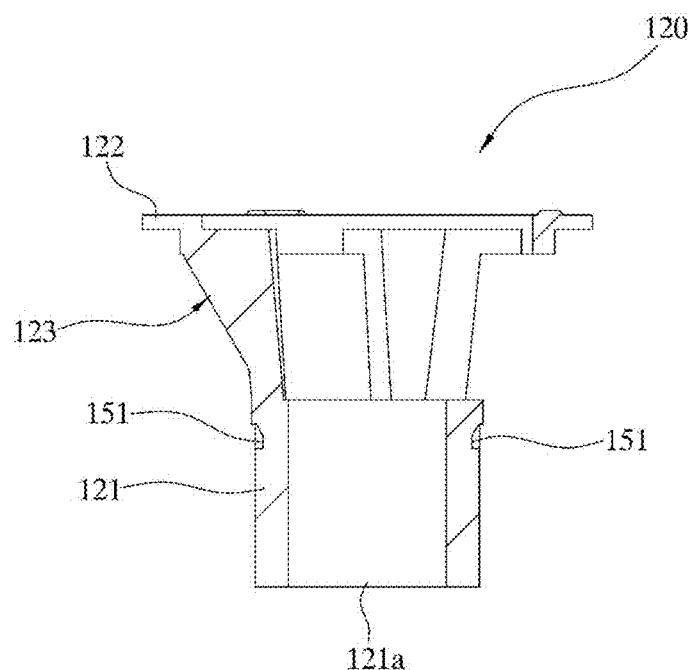
【FIG. 4a】
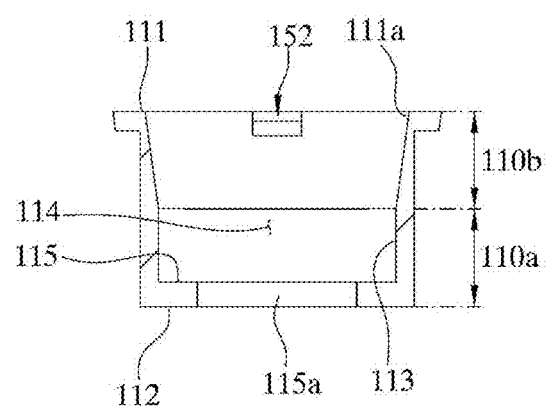

[FIG. 4b]
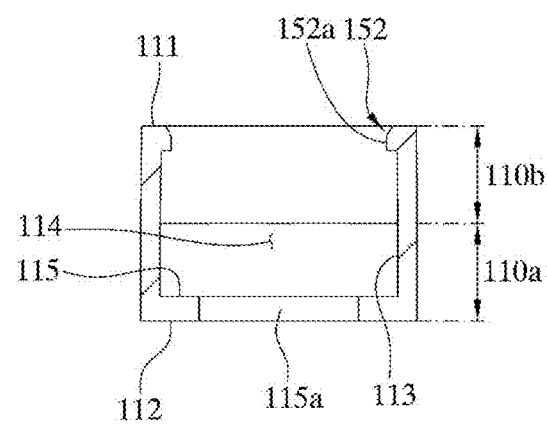
[FIG. 5]
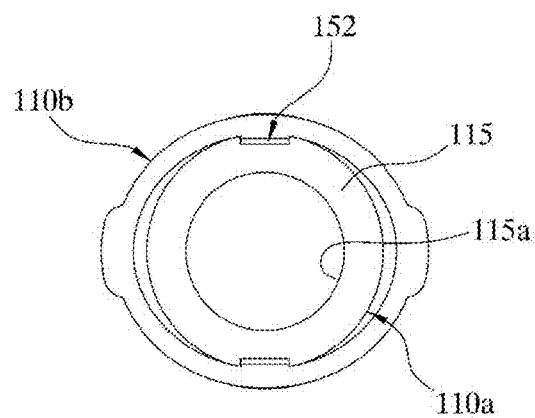

[FIG. 6]
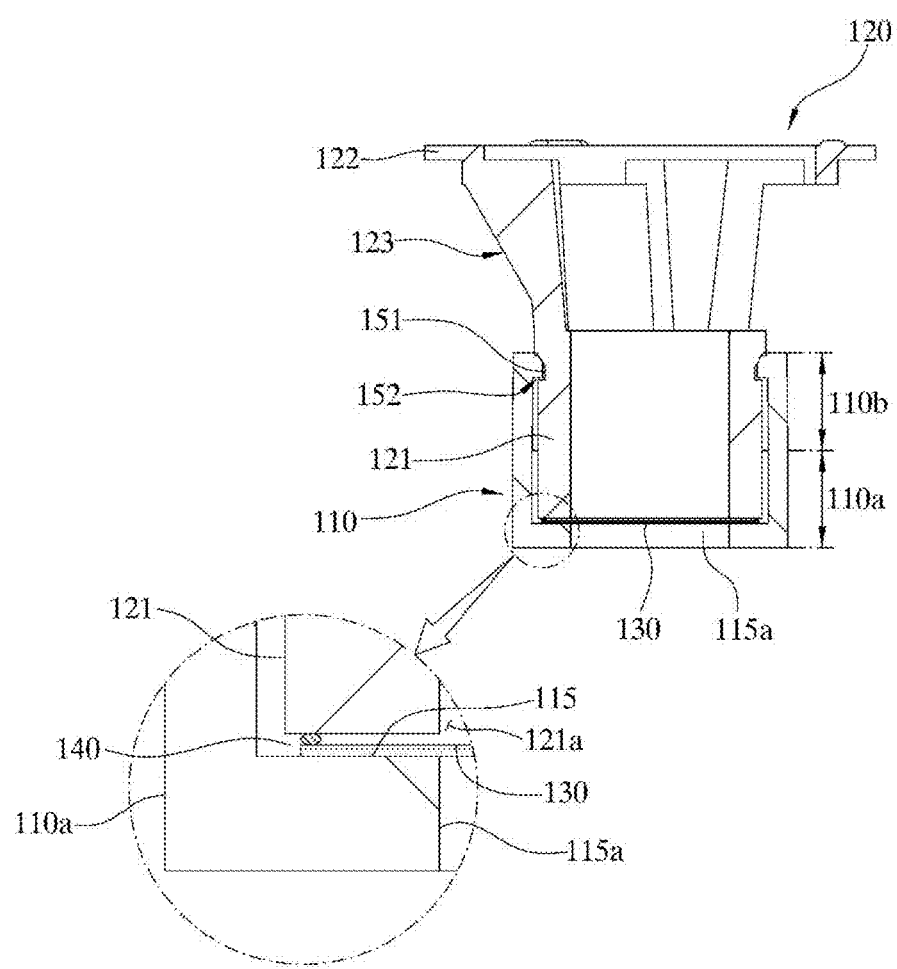

[FIG. 7]
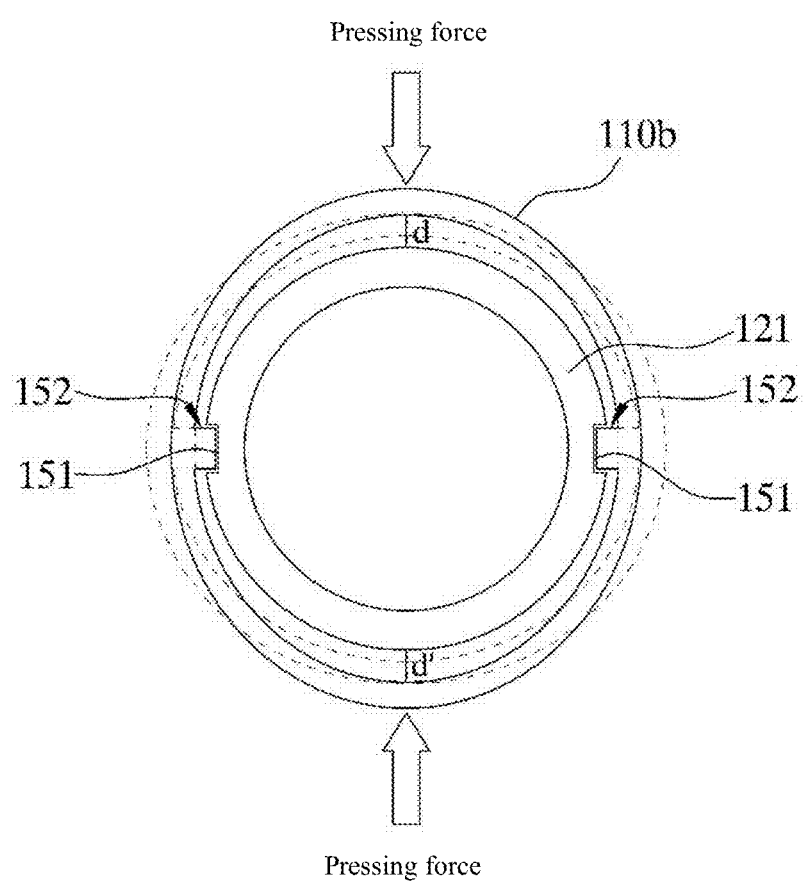

[FIG. 8]
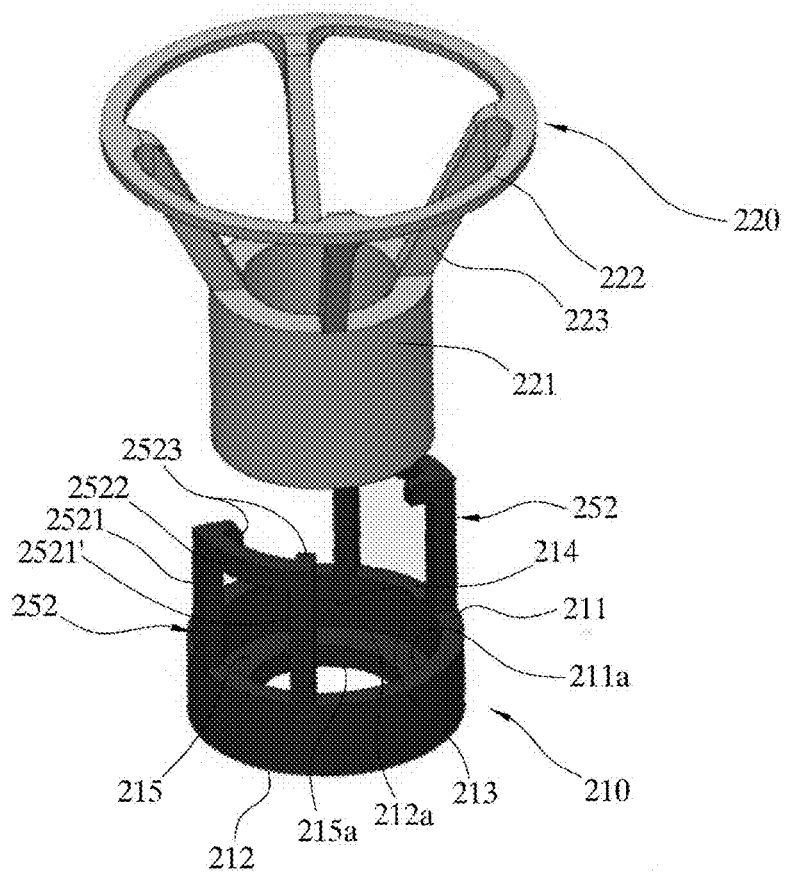

[FIG. 9]
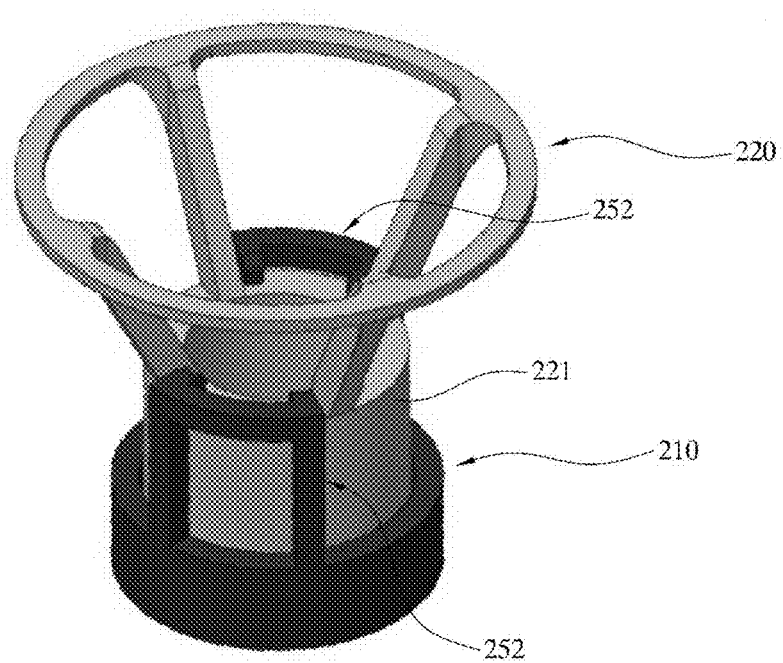

[FIG. 10]
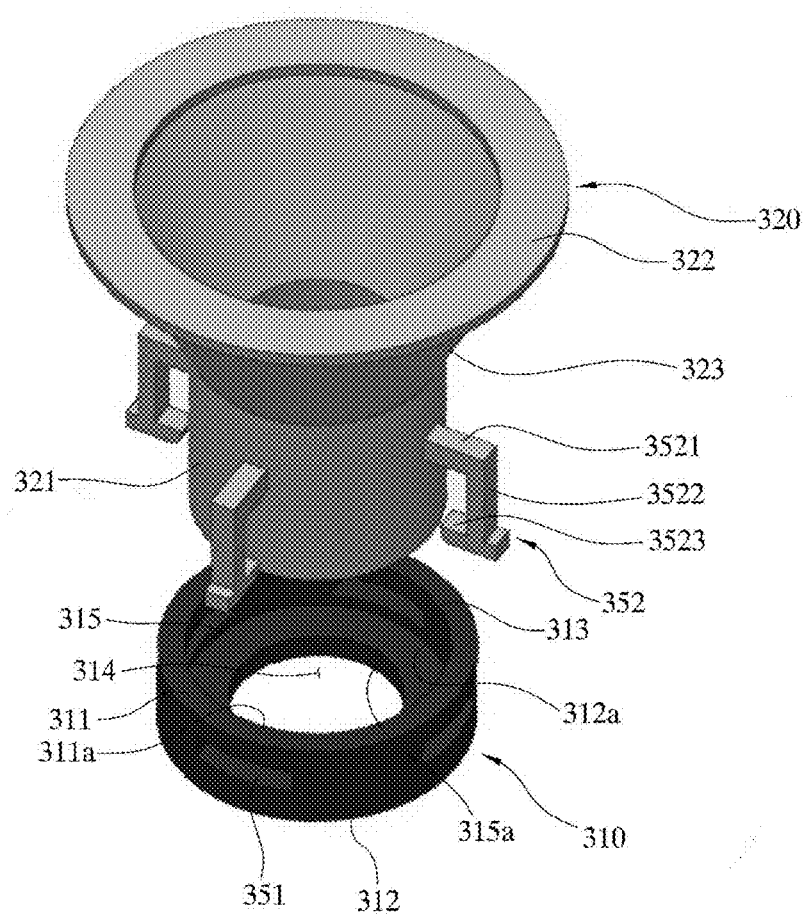

[FIG. 11]
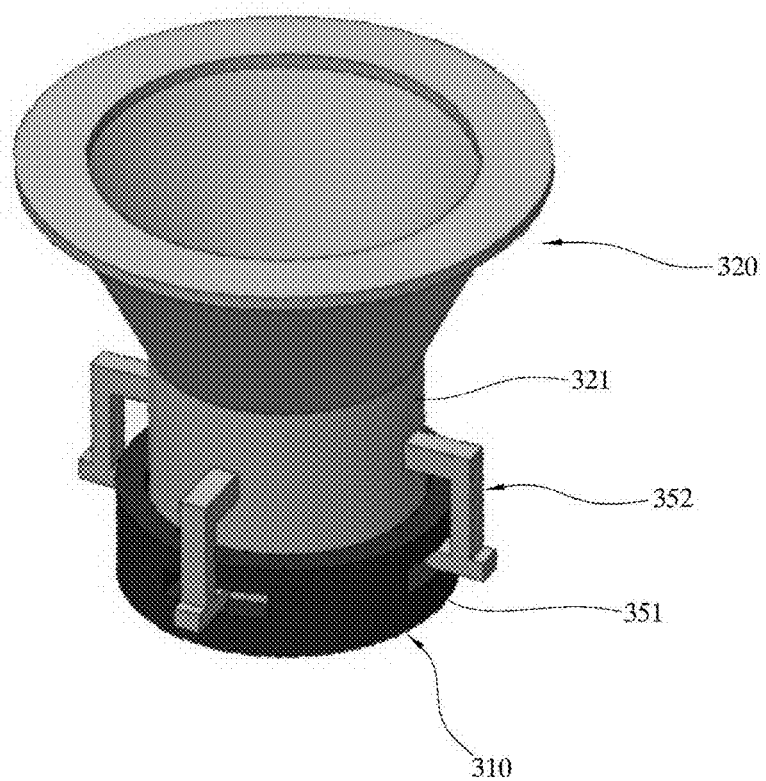

[FIG. 12]
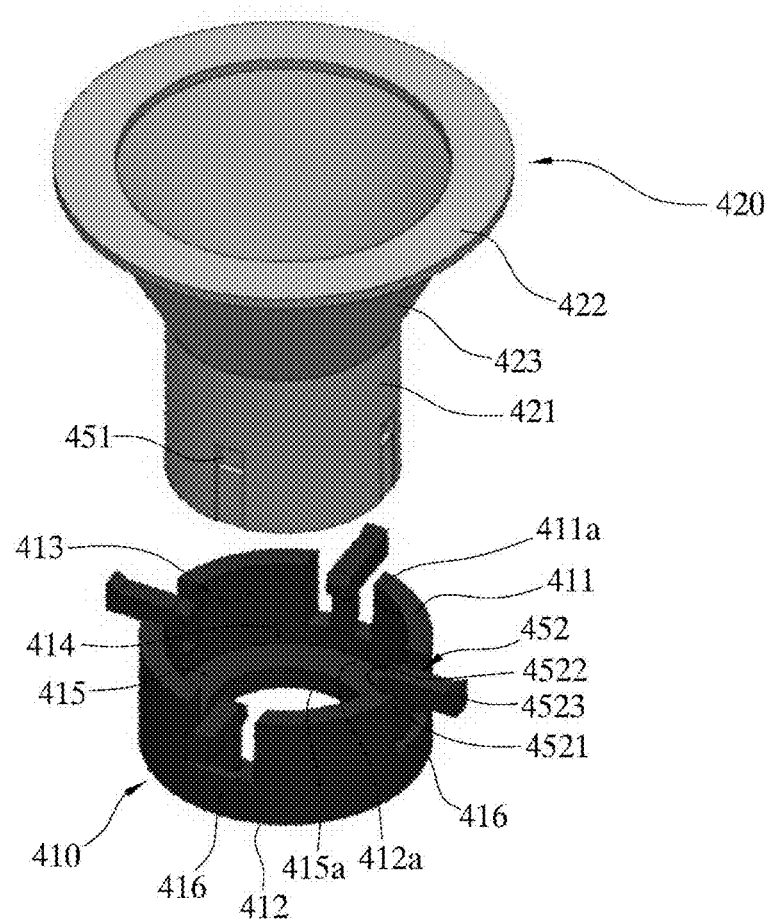

[FIG. 13]
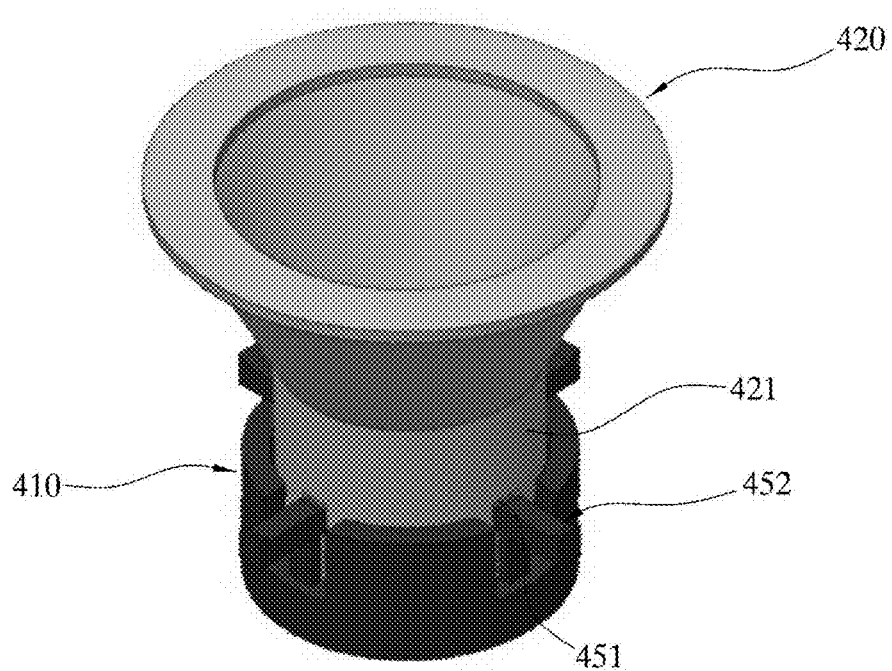

PERMEABLE MEMBRANE SUPPORT WITH A DETACHABLE PERMEABLE MEMBRANE

CROSS-REFERENCE TO RELATED APPLICATION

This application claims a benefit under 35 U.S.C. § 119(a) of Korean Patent Application No. 10-2020-0010770 filed on Jan. 30, 2020, on the Korean Intellectual Property Office, the entire disclosure of which is incorporated herein by reference for all purposes.

BACKGROUND

1. Field

The present disclosure relates to a permeable membrane support (PMS) referred to as a trans well.

2. Description of Related Art

A trans well or a permeable membrane support is used for vitro culture of tissues and organs and evaluation of functionality thereof in tissue engineering; for drug/toxin delivery in which potential drugs or toxins pass through a permeable membrane to observe cell responses; for studies of cell responses to drugs, environment, etc. using chemotactic responses of cells in a cell migration and invasion field; and for attaching different cells to upper and lower faces of a permeable membrane or culturing two or more different cells in a layered manner on an upper face thereof to realize functionality thereof in a cell co-culture field.

For example, different environments in terms of cell biology are created on upper and and lower faces of the permeable membrane. Then, whether the cell passes through the permeable membrane or not (referred to as cell migration or also referred to as chemotaxis) is evaluated to evaluate response or preference of the cell to the corresponding environment. In this case, a pore of the permeable membrane has a size of 3 to 8 μm which is a size suitable for the cell to pass therethrough.

Further, in PMS, cells are cultured in one of upper or lower culture dishes around the permeable membrane, while a specific substance (a wide variety of drugs, toxins, etc.) is contained in the other, thereby to observe response of the cell when the substance passes through the permeable membrane and is delivered to the cell. In this case, a pore of the permeable membrane is sized such that the cells cannot pass therethrough. The pore diameter may be 3 μm or smaller, generally, 1 to 0.4 μm.

In recent years, hydrogel is gelated on the permeable membrane of PMS for research of applications thereof (in which cells or drugs are encapsulated inside the gel).

In a general PMS, a permeable thin film made of PC, PET, and PTFE is attached to a lower face of a transparent support of a PS structure via bonding. As a result, when, after the culturing of the cells thereon, cell cultures are separated from the PMS, deformation of the PMS may occur. Thus, it is difficult to separate a sample containing the cells from the PMS in an intact layer form.

Further, when using the hydrogel, it is difficult to remove the culture sample from the PMS. Thus, in general, a spoon is used to remove a portion of the sample. However, this is problematic. Further, when the cells are used for evaluation while the cells are not separated therefrom, direct measurement using a microscope, etc. may not be available due to a size of the PMS.

Recently, there have been attempts to apply various conditions sequentially or to use the same tissue cultured on PMS for different studies as it is. However, in this case, a sequential test in different environments may not be achieved due to difficulty in separation of the cell.

It is difficult to separate a sample containing cells or tissues cultured on PMS, and hydrogel from PMS. Further, it is difficult to use the sample for various tests, measurements, and experiments while the sample is not detached from PMS but is attached thereto.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

A purpose of the present disclosure is to provide a new structure of a permeable membrane support (PMS) in which a permeable membrane is easily separated from the PMS.

Purposes in accordance with the present disclosure are not limited to the above-mentioned purpose. Other purposes and advantages in accordance with the present disclosure as not mentioned above may be understood from following descriptions and more clearly understood from embodiments in accordance with the present disclosure. Further, it will be readily appreciated that the purposes and advantages in accordance with the present disclosure may be realized by features and combinations thereof as disclosed in the claims.

One aspect of the present disclosure provides a permeable membrane support having an attachable and detachable permeable membrane, the permeable membrane support comprising: a lower support; an upper support partially accommodated into the lower support; and a permeable membrane disposed between the lower support and the upper support, wherein the lower support has a hollow cylinder shape having an outer diameter smaller than an inner diameter of a plate well such that the lower support is accommodated in the well of the plate, wherein the lower support has: a top having a first opening; a bottom having a second opening; an inner wall extending between the top and the bottom, wherein an inner open space is surrounded by the inner wall and communicates with the first and second openings; and a bottom support portion extending inwardly from the inner wall at a bottom of the lower support, wherein a central opening is defined in the bottom support portion and communicates with the inner space; wherein the upper support has: a cylindrical lower member fitted into the inner space of the lower support, wherein the cylindrical lower member has a bottom opening defined therein; an annular disk supported on a top of the well of the plate; and a bridge for connecting the cylindrical lower member and the annular disk with each other, wherein one of the upper support and the lower support has one of a hook having a projection and a groove to achieve snap-fit engagement therebetween, while the other of the upper support and the lower support has the other of the hook having the projection and the groove to achieve snap-fit engagement therebetween, wherein when the upper support and the lower support are engaged with each other in a snap-fit manner, the permeable membrane is sandwiched between the bottom opening of the cylindrical lower member of the upper support and a top face of the bottom support portion of the lower support.

In one implementation of the permeable membrane support, the permeable membrane includes a porous thin film, and a seal pattern bonded to the porous thin film.

In one implementation of the permeable membrane support, the seal pattern includes a circular pattern extending along an outer edge of the porous thin film, wherein when the upper support and the lower support are engaged with each other in a snap-fit manner, the seal pattern is sandwiched between the bottom opening of the cylindrical lower member of the upper support and the top face of the bottom support portion of the lower support.

In one implementation of the permeable membrane support, the permeable membrane support further comprises a seal disposed on a top face or a bottom face of the permeable membrane and extending along an outer perimeter of the permeable membrane.

In one implementation of the permeable membrane support, the lower support includes a cylindrical lower portion and an elliptical upper portion, wherein the first opening is elliptical, and the second opening is circular, wherein the hook includes two opposing hooks extending inwards respectively from both opposing points of the inner wall in a short-axis direction of a top of the elliptical upper portion, wherein the groove includes two opposing grooves defined in an outer face of the cylindrical lower member to receive the two hooks therein respectively in a snap-fit manner.

In one implementation of the permeable membrane support, the hook includes at least two hooks extending upwards from a top face of the lower support, wherein each of the at least two opposing hooks is constructed to be coupled to a top of the cylindrical lower member of the upper support in a snap-fit manner.

In one implementation of the permeable membrane support, the hook includes at least two hooks, each hook having a horizontal extension extending outwardly horizontally from an outer face of the cylindrical lower member of the upper support and a vertical extension extending downwardly from an outer end of the horizontal extension, wherein the groove includes at least two grooves defined in an outer face of the lower support to receive the at least two hooks therein respectively in a snap-fit manner.

In one implementation of the permeable membrane support, the lower support has at least two cut-aways, wherein each cut-away is formed by partially cutting away an upper portion of the lower support around each of at least two hooks, wherein each cut-away has an inverse U shape, wherein each hook extends upwardly from a center of a bottom of each cut-away, wherein the groove includes at least two grooves defined in an outer face of the cylindrical lower member of the upper support to receive the at least two hooks therein respectively in a snap-fit manner.

Effects in accordance with the present disclosure may be as follows but may not be limited thereto.

When using the permeable membrane support (PMS) with the attachable and detachable permeable membrane according to the present disclosure, the permeable membrane may be safely and independently separated from the PMS. Thus, when culturing cells on the PMS and then separating the cell culture from the PMS, the permeable membrane having the cultured cells thereon may be separated from the PMS in an intact layer form while deforming the permeable membrane. Then, the separated permeable membrane is placed on a stage of a microscope and then the culture sample on the permeable membrane is directly measured using the microscope.

Further, due to the snap-fit coupling structure between the upper support and lower support, easy coupling and separation therebetween may be easy. Thus, the coupling and separation between the upper support and lower support may be achieved simply.

In addition to the effects as described above, specific effects in accordance with the present disclosure will be described together with the detailed description for carrying out the disclosure.

BRIEF DESCRIPTION OF DRAWINGS

FIG. 1 is an exploded perspective view for illustrating a configuration of a permeable membrane support having an attachable and detachable permeable membrane according to a first embodiment of the present disclosure.

FIG. 2 is a bottom exploded perspective view of a lower support and an upper support as shown in FIG. 1.

FIG. 3 is a vertical side elevation view of the upper support shown in FIG. 1 having a groove for snap-fit engagement.

FIG. 4A is a vertical cross-sectional view of the lower support shown in FIG. 1 as taken in a line extending in a long-axis direction of an elliptical upper portion of the lower support.

FIG. 4B is a vertical cross-sectional view of the lower support shown in FIG. 1 as taken in a line extending in a short-axis direction of an elliptical upper portion of the lower support.

FIG. 5 is a plan view of the lower support shown in FIG. 1.

FIG. 6 is a cross-sectional view showing a state in which components of the permeable membrane support having the attachable and detachable permeable membrane according to the first embodiment of the present disclosure are combined with each other.

FIG. 7 is a diagram schematically showing an elliptical upper portion of the lower support and a cylindrical lower member inserted through the elliptical upper portion into the lower support for illustration of a separation process between the upper support and lower support shown in FIG. 1.

FIG. 8 is an exploded perspective view for illustrating a configuration of a permeable membrane support having an attachable and detachable permeable membrane according to a second embodiment of the present disclosure.

FIG. 9 is a view showing a state in which components of the permeable membrane support having the attachable and detachable permeable membrane according to the second embodiment of the present disclosure are combined with each other.

FIG. 10 is an exploded perspective view for illustrating a configuration of a permeable membrane support having an attachable and detachable permeable membrane according to a third embodiment of the present disclosure.

FIG. 11 is a view showing a state in which components of the permeable membrane support having the attachable and detachable permeable membrane according to the third embodiment of the present disclosure are combined with each other.

FIG. 12 is an exploded perspective view for illustrating a configuration of a permeable membrane support having an attachable and detachable permeable membrane according to a fourth embodiment of the present disclosure.

FIG. 13 is a view showing a state in which components of the permeable membrane support having the attachable and detachable permeable membrane according to the fourth embodiment of the present disclosure are combined with each other.

DETAILED DESCRIPTIONS

For simplicity and clarity of illustration, elements in the figures are not necessarily drawn to scale. The same reference numbers in different figures represent the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to limit the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" or "beneath" a second element or layer, the first element may be disposed directly on or beneath the second element or may be disposed indirectly on or beneath the second element with a third element or layer being disposed between the first and second elements or layers.

It will be understood that when an element or layer is referred to as being "connected to", or "coupled to" another element or layer, it may be directly on, connected to, or coupled to the other element or layer, or one or more intervening elements or layers may be present. In addition, it will also be understood that when an element or layer is referred to as being "between" two elements or layers, it may be the only element or layer between the two elements or layers, or one or more intervening elements or layers may also be present.

Further, as used herein, when a layer, film, region, plate, or the like is disposed "on" or "on a top" of another layer, film, region, plate, or the like, the former may directly contact the latter or still another layer, film, region, plate, or the like may be disposed between the former and the latter. As used herein, when a layer, film, region, plate, or the like is directly disposed "on" or "on a top" of another layer, film, region, plate, or the like, the former directly contacts the latter and still another layer, film, region, plate, or the like is not disposed between the former and the latter. Further, as used herein, when a layer, film, region, plate, or the like is disposed "below" or "under" another layer, film, region, plate, or the like, the former may directly contact the latter or still another layer, film, region, plate, or the like may be disposed between the former and the latter. As used herein, when a layer, film, region, plate, or the like is directly disposed "below" or "under" another layer, film, region, plate, or the like, the former directly contacts the latter and still another layer, film, region, plate, or the like is not disposed between the former and the latter.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

First Embodiment

FIG. 1 is an exploded perspective view for illustrating a configuration of a permeable membrane support having an attachable and detachable permeable membrane according to a first embodiment of the present disclosure. FIG. 2 is a bottom exploded perspective view of a lower support and an upper support as shown in FIG. 1. FIG. 3 is a vertical side elevation view of the upper support shown in FIG. 1 having a groove for snap-fit engagement. FIG. 4A is a vertical cross-sectional view of the lower support shown in FIG. 1 as taken in a line extending in a long-axis direction of an elliptical upper portion of the lower support. FIG. 4B is a vertical cross-sectional view of the lower support shown in FIG. 1 as taken in a line extending in a short-axis direction of an elliptical upper portion of the lower support. FIG. 5 is a plan view of the lower support shown in FIG. 1. FIG. 6 is a cross-sectional view showing a state in which components of the permeable membrane support having the attachable and detachable permeable membrane according to the first embodiment of the present disclosure are combined with each other. FIG. 7 is a diagram schematically showing an elliptical upper portion of the lower support and a cylindrical lower member inserted through the elliptical upper portion into the lower support for illustration of a separation process between the upper support and lower support shown in FIG. 1.

Referring to FIG. 1 to FIG. 5, the permeable membrane support having the attachable and detachable permeable membrane according to the first embodiment of the present disclosure includes a lower support 110, an upper support 120, a permeable membrane 130, and a seal 140. The seal may be embodied as a seal pattern bonded to the permeable membrane or as a separate seal not joined to the permeable membrane.

The lower support 110 may have a hollow cylinder shape having a smaller outer diameter than an inner diameter of a plate well (not shown) as described in the prior art so as to be accommodated in the plate well.

The lower support 110 of the hollow cylinder shape may include a top 111 with a first opening 111a, a bottom 112 with a second opening 112a, and an inner wall 113 extending between the first opening 111a and the second opening 112a and defining an inner space 114 communicating with the first opening 111a and the second opening 112a.

Further, the lower support 110 may include a bottom support portion 115 extending inwards from the inner wall 113 at the bottom 112 and defining a central opening 115a communicating with the inner space 114.

The upper support 120 may include an cylindrical lower member 121, an annular disk 122, and a bridge 123.

The cylindrical lower member 121 constitutes a lower portion of the upper support 120, and has an outer diameter sized such that the member 112 is fitted inside the inner space 114 of the lower support 110.

The annular disk 122 defines an upper portion of the upper support 120, and has an inner diameter and an outer diameter larger than an outer diameter of the cylindrical lower member 121. This annular disk 122 is supported on a top of the plate well so that the permeable membrane support is retained in the plate well.

The bridge 123 connects the cylindrical lower member 121 and the annular disk 122 to each other. In one example, the bridge 123 includes a disk connection portion 1231 protruding from an inner face of annular disk 122 inwardly and having an approximately fan-shaped shape, a lower member connection portion 1232 extending vertically from a distal end of the disk connection portion 1231 toward the cylindrical lower member 121, and a triangular strength enhancing portion 1233 disposed between a bottom face of the disk connection portion 1231 and an outer face of the lower member connection portion 1232 to enhance a strength of a bent boundary portion between the lower member connection portion 1232 and the disk connection portion 1231 to prevent breakage between disk connection portion 1231 and lower member connection portion 1232. The bridge 123 may include a plurality of bridges arranged along a circumferential direction of the annular disk 122. For example, the number of the bridges 123 may be three. In this case, an opening 1234 is defined between adjacent bridges 123. Air may flow through the opening 1234 and a medium may be supplied therethrough.

The permeable membrane 130 may be disposed between the lower support 110 and the upper support 120, and may be embodied as a porous thin film.

The seal 140 may be embodied as a pattern located on the top face or the bottom face of the permeable membrane 130 and may extend along a circumference thereof. The seal may be embodied as a seal pattern bonded to one or both faces of the permeable membrane, or may contact a face of the permeable membrane without being bonded to the permeable membrane. Alternatively, the seal 140 may surround an edge of the permeable membrane 130 so as to be located on both the top face and the bottom face of the edge of the permeable membrane 130. For example, the seal 140 may be made of a silicone material.

When the lower support 110 and the upper support 120 are engaged with each other in a snap-fit manner, the permeable membrane 130 and the seal 140 may be interposed between and contact the opening 121a of the cylindrical lower member 121 of the upper support 120 and the bottom support portion 115 of the lower support 110. In this connection, the permeable membrane 130 covers the central opening 115a of the bottom support portion 115.

In one example, the upper support 120 and the lower support 110 may be combined with each other in a snap-fit manner. To this end, the upper support 120 and the lower support 110 may have a hook 152 having a projection 152a and a groove 151 respectively. Alternatively, the upper support 120 and the lower support 110 may have a groove 151 and a hook 152 having a projection 152a respectively.

In one example, the upper support 120 may include the groove 151, and the lower support 110 may include the hook 152. However, the present disclosure is not limited thereto.

In this case, the hook 152 may include two opposing hooks 152 extending inwards respectively from both ends of an inner wall of the lower support 110 in a short-axis direction of the elliptical upper portion 110b of the lower support 110. In this connection, each hook 152 has a projection 152a.

The upper support 120 may include two opposing grooves 151 defined in the outer face of the cylindrical lower member 121 for snap-fit engagement with the corresponding two hooks 152.

In this connection, a location where the hook 152 and groove 151 are joined with each other is determined such that the permeable membrane 130 and the seal 140 may be interposed between and contact the opening 121a of the cylindrical lower member 121 of the upper support 120 and the top face of the bottom support portion 115 of the lower support 110. The location may be arbitrarily set by those skilled in the art based on thicknesses of the permeable membrane 130 and the seal 140.

In one example, the lower support 110 may include an cylindrical lower portion 110a and an elliptical upper portion 110b. The first opening 111a of the lower support 110 is defined in the elliptical upper portion 110b and thus is elliptical, while the second opening 112a of the lower support 110 is defined in the cylindrical lower portion 110a and is circular.

In this connection, an short-axis A of the first opening 111a has a diameter greater than an outer diameter of the cylindrical lower member 121 of the upper support 120, while a long-axis direction B of the first opening 111a has a length sized such that each of the two hooks 152 is spaced from each of the two grooves 151.

That is, a length of the long-axis B of the first opening 111a is sized such that each of a distance d between a first point as one end of the long-axis direction B of the first opening 111a and an outer face of the cylindrical lower member 121 inserted into the lower support 110, and a distance d' between a second point opposite the first point and the outer face of the cylindrical lower member 121 inserted into the lower support 110 is larger than or equal to an insertion depth by which the projection 152a of each of the two hooks 152 is inserted into each of the two grooves 151.

Hereinafter, a process in which the lower support 110, the upper support 120, the permeable membrane 130 and the seal 140 of the permeable membrane support having the attachable and detachable permeable membrane according to the first embodiment of the present disclosure are assembled with each other, and a process in which the upper support 120 and the lower support 110 are separated from each other will be described.

Assembly Process

First, the permeable membrane 130 and the seal 140 are inserted into the lower support 110 through the first opening 111a of the elliptical upper portion 110b of the lower support 110 and are placed on the top face of the bottom support portion 115.

Subsequently, the cylindrical lower member 121 of the upper support 120 is inserted into the elliptical upper portion 110b of the lower support 110 and the cylindrical lower portion 110a through the first opening 111a of the elliptical upper portion 110b of the lower support 110. In this connection, the two hooks 152 located on the inner wall of the elliptical upper portion 110b of the lower support 110 are pushed to be spaced further away from each other such that a length of the short-axis direction of the elliptical upper portion 110b further increases. The cylindrical lower member 121 is inserted into the elliptical upper portion 110b of the lower support 110 and the cylindrical lower portion 110a such that the opening 121a thereof reaches the permeable membrane 130 or the seal 140. Thus, the two grooves 151 of the cylindrical lower member 121 have the same vertical level as those of the two hooks 152 located on the inner wall of the elliptical upper portion 110b. Then, a length of the short-axis direction of the elliptical upper portion 110b of the elongated cylindrical lower member 121 reduces, so that each hook 152 may be engaged with each groove 151.

As shown in FIG. 6, when the upper support 120 and the lower support 110 are engaged with each other, the permeable membrane 130 and the seal 140 may be interposed between and contact the top face of the bottom support portion 115 of the lower support 110 and the opening face 121a of the cylindrical lower member 121 of the upper support 120.

Separation Process

When a user intends to separate the upper support 120 and the lower support 110 from each other, a user pushes opposing points in the long-axis direction B of the elliptical upper portion 110b of the lower support 110 toward the center of the lower support 110, such that inners faces of the opposing points in the long-axis direction B of the elliptical upper portion 110b contact the outer face of the cylindrical lower member 121 inserted into the lower support 110, as shown in FIG. 7. Thus, each of the two hooks 152 coupled to each of the two grooves 151 of the cylindrical lower member 121 is spaced apart from each of the two grooves 151 and is positioned out of each of the two grooves 151. In this state, when the upper support 120 is pulled upward, the upper support 120 may be separated from the interior of the lower support 110.

In this way, only the permeable membrane 130 is placed on the bottom support portion 115 of the lower support 110. Thus, only the permeable membrane 130 is independently separated from the lower support 110.

Second Embodiment

FIG. 8 is an exploded perspective view for illustrating a configuration of a permeable membrane support having an attachable and detachable permeable membrane according to a second embodiment of the present disclosure. FIG. 9 is a view showing a state in which components of a permeable membrane support having an attachable and detachable permeable membrane according to a second embodiment of the present disclosure are combined with each other.

Referring to FIG. 8 and FIG. 9, the permeable membrane support with the attachable and detachable permeable membrane according to the second embodiment of the present disclosure includes a lower support 210, an upper support 220, a permeable membrane (not shown), and a seal (not shown).

The structure of each of the permeable membrane and the seal in the second embodiment is the same as or similar to that of each of the permeable membrane 130 and the seal 140 of the permeable membrane support having the attachable and detachable permeable membrane according to the first embodiment of the present disclosure as described with reference to FIG. 1. Thus, descriptions thereof will be omitted.

The lower support 210 has a hollow cylinder shape. The support 210 has a top 211 with a first opening 211a, a bottom 212 with a second opening 212a, and an inner wall 213 extending the first opening 211a and the second opening 212a, and defining an inner space 214 communicating with the first opening 211a and the second opening 212a.

Further, the lower support 210 may include a bottom support portion 215 extending inward from the inner wall 213 of the bottom 212 and including a central opening 215a communicating with the inner space 214.

The upper support 220 may include a cylindrical lower member 221, an annular disk 222, and a bridge 223.

A structure of each of the cylindrical lower member 221 and the annular disk 222 is the same as that of each of the cylindrical lower member 121 and the annular disk 122 of the permeable membrane support having an attachable and detachable permeable membrane according to the first embodiment of the present disclosure. Detailed descriptions thereof will be omitted.

The bridge 223 connects the cylindrical lower member 221 and the annular disk 222 to each other. In one example, the bridge 223 may be embodied as a bar inclinedly extending from an inner face of the annular disk 222 having the larger diameter toward the top of the cylindrical lower member 221 having a diameter smaller than that of the annular disk 222. A plurality of bridges 223 may be arranged along the circumferential direction of the annular disk 222 and the cylindrical lower member 221. For example, the number of the bridges 223 may be four. In this connection, an opening is defined between adjacent bridges 223. The top of the cylindrical lower member 221 may be exposed through the opening.

In one example, the upper support 220 and lower support 210 may be coupled to each other in a snap-fit manner. To this end, the lower support 210 may include two or more opposing hooks 252 extending upward from the top face of the top 211 and coupled in a snap-fit manner to the top of the cylindrical lower member 221 of the upper support 220.

In one example, each hook 252 has a first support bar 2521 and a second support bar 2521' extending upward from the top face of the top 211 of the lower support 210, a connector 2522 connecting tops of the first support bar 2521 and the second support bar 2521' to each other, and a pair of projections 2523 projecting inwardly from both ends of the inner face of the connector 2522 respectively. Two hooks 252 may be provided. The two hooks 252 may be opposite to each other. A spacing between the first support bar 2521 and the second support bar 2521' may be equal to or smaller than a spacing between the adjacent bridges 223.

In this connection, a position where the hook 252 is coupled to the top of the cylindrical lower member 221 is determined such that the permeable membrane and the seal are interposed between and contact the opening (not shown) of the cylindrical lower member 221 of the upper support 220 and the top face of the bottom support portion 215 of the lower support 210. This position may be arbitrarily set by those skilled in the art based on thicknesses of the permeable membrane and the seal.

Hereinafter, a process in which the lower support 210, the upper support 220, the permeable membrane and the seal of the permeable membrane support having the attachable and detachable permeable membrane according to the second embodiment of the present disclosure are assembled with each other, and a process in which the upper support 220 and the lower support 210 are separated from each other will be described.

Assembly Process

First, the permeable membrane and the seal are inserted into the lower support 210 through the first opening 211a of the top 211 of the lower support 210 and are placed on the top face of the bottom support portion 215.

Subsequently, the cylindrical lower member 221 of the upper support 220 is inserted into the lower support 210 through the first opening 211a of the top 211 of the lower support 210. In this connection, the two hooks 252 extending from the top 211 of the lower support 210 are pushed outwardly to be spaced further apart from each other. Then, the opening of the cylindrical lower member 221 reaches the permeable membrane or the seal. Then, the spacing between the two hooks 252 is reduced in an elastic manner such that each projection 2523 is coupled to the top of the cylindrical lower member 221 as shown in FIG. 9.

In this way, the upper support 220 and the lower support 210 are coupled to each other, such that the permeable membrane and the seal are interposed between the top face of the bottom support portion 215 of the lower support 210 and the opening of the cylindrical lower member 221 of the upper support 220.

Separation Process

When a user wants to separate the upper support 220 and the lower support 210 from each other, the user holds the connectors 2522 of the two hooks 252 on the lower support 210 and pulls the connectors 2522 away from each other. Thus, the projection 2523 of each hook 252 is spaced from the top of the cylindrical lower member 221. In this state, the upper support 220 is pulled upwards, such that the upper support 220 is separated from the interior of the lower support 210.

In this way, only the permeable membrane is placed on the bottom support portion 215 of the lower support 210. Then, only the permeable membrane is separated independently from the lower support 210.

Third Embodiment

FIG. 10 is an exploded perspective view for illustrating a configuration of a permeable membrane support having an attachable and detachable permeable membrane according to a third embodiment of the present disclosure. FIG. 11 is a view showing a state in which components of a permeable membrane support having an attachable and detachable permeable membrane according to a third embodiment of the present disclosure are combined with each other.

Referring to FIG. 10 and FIG. 11, the permeable membrane support having an attachable and detachable permeable membrane according to a third embodiment of the present disclosure includes a lower support 310, an upper support 320, a permeable membrane (not shown) and a seal (not shown).

The structure of each of the permeable membrane and the seal is the same as or similar to that of each of the permeable membrane 130 and the seal 140 of the permeable membrane support having the attachable and detachable permeable membrane according to the first embodiment of the present disclosure as described with reference to FIG. 1. Thus, descriptions thereof will be omitted.

The lower support 310 has a hollow cylinder shape. The support 310 has a top 311 with a first opening 311a, a bottom 312 with a second opening 312a, and an inner wall 313 extending between the first opening 311a and the second opening 312a, and defining an inner space 314 communicating with the first opening 311a and the second opening 312a.

Further, the lower support 310 may include a bottom support portion 315 extending inward from the inner wall 313 of the bottom 312 and including a central opening 315a communicating with the inner space 314.

The upper support 320 may include a cylindrical lower member 321, and annular disk 322, and a bridge 323.

A structure of each of the cylindrical lower member 321 and the annular disk 322 is the same as that of each of the cylindrical lower member 121 and the annular disk 122 of the permeable membrane support having an attachable and detachable permeable membrane according to the first embodiment of the present disclosure. Detailed description thereof will be omitted.

The bridge 323 connects the cylindrical lower member 321 and the annular disk 322 with each other.

In one example, the bridge 323 may be embodied as a substantially funnel shaped structure extending in a tapered manner from the annular disk 322 having a larger dimeter toward the top of the cylindrical lower member 321 having a smaller diameter than that of the annular disk 322.

In one example, the upper support 320 and the lower support 310 may be snap-fit coupled to each other. To this end, the upper support 320 may include a hook 352 having a projection 3523. The lower support 310 may have a groove 351. Alternatively, the lower support 310 may include a hook 352 having a projection 3523. The upper support 320 may have a groove 351.

In one example, the lower support 310 may include two or more hooks 352, and the upper support 320 may include two or more corresponding grooves 351.

The hook 352 may extend outwardly by a predetermined length in a perpendicular direction to the outer wall of the cylindrical lower member 321 therefrom and then may be bend downwardly. In this case, each hook 352 has a horizontal extension 3521 outwardly extending from the outer wall of the cylindrical lower member 321, a vertical extension 3522 bent downward from a distal end of the horizontal extension 3521 and extending downwardly, and a projection 3523 protruding inwardly toward the outer wall of the cylindrical lower member 321 from the distal end of the vertical extension 3522. A protruding length of the projection 3523 is sized such that a tip of the projection overlaps an edge of the top 311 of the lower support 310, and a bottom face of the projection may have a curved shape. The hooks 352 may be arranged along the circumferential direction of the cylindrical lower member 321. For example, the number of the hooks may be four.

The groove 351 may be defined in the outer wall of the lower support 310 at a vertical level corresponding to a vertical level of the corresponding projection 3523 in a state in which the cylindrical lower member 321 is inserted into the lower support 310 so that the permeable membrane and the seal are sandwiched between the opening (not shown) of the cylindrical lower member 321 and the top face of the bottom support portion 315 of the lower support 310. The grooves 351 may be arranged along the circumferential direction of the hollow cylinder shape of the lower support 310. The number of the grooves may be, for example, four. The shape of the groove 351 is not particularly limited, and may have, for example, a rectangular shape extending in a circumferential direction of the hollow cylinder member.

Hereinafter, a process in which the lower support 310, the upper support 320, the permeable membrane and the seal of the permeable membrane support having the attachable and detachable permeable membrane according to the third embodiment of the present disclosure are assembled with each other, and a process in which the upper support 320 and the lower support 310 are separated from each other will be described.

Assembly Process

First, the permeable membrane and the seal are inserted into the lower support 310 through the first opening 311a of the top 311 of the lower support 310 and are placed on the top face of the bottom support portion 315.

Subsequently, the cylindrical lower member 321 of the upper support 320 is inserted into the lower support 310 through the first opening 311a of the top 311 of the lower support 310. In this connection, a bottom of the projection 3523 of each hook 352 extending from the outer wall of the cylindrical lower member 321 is pushed against the edge of the top 311 of the lower support 310 via a pressing force to insert the cylindrical lower member 321 into the lower support while the bottom of the projection 3523 of each hook 352 contacts the edge of the top 311 of the lower support 310. Thus, the vertical extension 3522 and the projection 3523 of each hook 352 are moved outwardly away from the outer wall of the cylindrical lower member 321. The opening of the cylindrical lower member 321 reaches the permeable membrane or the seal. Then, each hook 352 is displaced inwardly in an elastic manner and is engaged with each groove 351 of the lower support 310 as shown in FIG. 11.

As such, the upper support 320 and the lower support 310 are fastened to each other, such that the permeable membrane and the seal are sandwiched between the top face of the bottom support portion 315 of the lower support 310 and the opening of the cylindrical lower member 321 of the upper support 320.

Separation Process

When a user wants to separate the upper support 320 and the lower support 310 from each other, the user holds the vertical extensions 3522 of the two hooks 352 adjacent to each other or the two hooks 352 opposite to each other among the four hooks 352 of the upper support 320, and pull the two vertical extensions 3522 to be spaced away from the grooves 351. Thus, the projections 3523 of the two hooks 352 are separated from the grooves 351. Subsequently, when remaining two hooks 352 are pulled away from the grooves 351 in the same way, the projections thereof are separated from the grooves 351. In this state, the upper support 320 is pulled upward or the lower support 310 is pulled downward, such that the upper support 320 and the lower support 310 are separated from each other.

In this way, only the permeable membrane is placed on the bottom support portion 315 of the lower support 310. Then, only the permeable membrane is separated from the lower support 310 independently.

Fourth Embodiment

FIG. 12 is an exploded perspective view for illustrating a configuration of a permeable membrane support having an attachable and detachable permeable membrane according to a fourth embodiment of the present disclosure. FIG. 13 is a view showing a state in which components of a permeable membrane support having an attachable and detachable permeable membrane according to a fourth embodiment of the present disclosure are combined with each other.

Referring to FIG. 12 and FIG. 13, the permeable membrane support with the attachable and detachable permeable membrane according to the fourth embodiment of the present disclosure includes a lower support 410, an upper support 420, a permeable membrane (not shown) and a seal (not shown).

The structure of each of the permeable membrane and the seal is the same as or similar to that of each of the permeable membrane 130 and the seal 140 of the permeable membrane support having the attachable and detachable permeable membrane according to the first embodiment of the present disclosure as described with reference to FIG. 1. Thus, descriptions thereof will be omitted.

The lower support 410 has a hollow cylinder shape and has a top 411 having a first opening 411a, a bottom 412 having a second opening 412a and an inner wall 413 extending between the first opening 411a and the second opening 412a and defining an inner space 414 communicating with the first opening 411a and the second opening 412a.

Further, the lower support 410 may include a bottom support portion 415 extending inward from the inner wall 413 of the bottom 412 and including a central opening 415a communicating with the inner space 414.

The upper support 420 may include a cylindrical lower member 421, an annular disk 422, and a bridge 423.

A structure of each of the cylindrical lower member 421 and the annular disk 422 is the same as that of each of the cylindrical lower member 121 and the annular disk 122 of the permeable membrane support having an attachable and detachable permeable membrane according to the first embodiment of the present disclosure. Thus, detailed description thereof will be omitted.

The bridge 423 connects the cylindrical lower member 421 and the annular disk 422 to each other.

In one example, the bridge 423 may be embodied as a substantially funnel shaped structure extending in a tapered manner from the annular disk 422 having a larger dimeter toward the top of the cylindrical lower member 421 smaller in diameter than that of the annular disk 422.

In one example, the upper support 420 and the lower support 410 may be snap-fit combined with each other. To this end, the upper support 420 and the lower support 410 may include a hook 452 having a projection 4523 and a groove 451 respectively or vice versa.

In one example, the upper support 420 may include the groove 451, and the lower support 410 may include a cut-away 416 and the hook 452.

The grooves 451 may be defined in the outer face of the cylindrical lower member 421 of the upper support 420 and may be arranged along the circumferential direction of the cylindrical lower member 421 of the upper support 420. The number of the grooves may be, for example, four.

Each cut-away 416 extends downward from the top 411 of the lower support 410 in an inverse U shape. That is, an upper portion of the lower support 410 is cut away around each hook 452. Thus, each cut-away 416 has the inverse U shape. The number of the cut-aways may be two or more. For example, the four cut-aways 416 may be arranged along the circumferential direction of the lower support 410.

The number of the hook 452 may be, for example, four. Each hook 452 has a vertical extension 4521 extending upward from a bottom of each of the four cut-aways 416, a horizontal extension 4522 extending horizontally outwardly from a top of the vertical extension 4521, and a projection 4523 protruding inwardly from one end of the horizontal extension 4522 connected to the vertical extension 4521. A top of the projection 4523 may have a curved shape. A protruding length of the projection 4523 may be sized such that an end of the projection overlaps an edge of the bottom of the cylindrical lower member 421.

In this connection, a position where the hook 452 and the groove 451 are engaged with each other may be determined such that the permeable membrane and the seal are sandwiched between the opening (not shown) of the cylindrical lower member 421 of the upper support 420 and the top face of the bottom support portion 415 of the lower support 410. This position may be arbitrarily set by those skilled in the art based on the thicknesses of the permeable membrane and the seal.

Hereinafter, a process of assembling the lower support 410, the upper support 420, the permeable membrane and the seal of the permeable membrane support having attachable and detachable permeable membrane according to the second embodiment of the present disclosure with each other and a process of separating the upper support 420 and the lower support 410 from each other will be described.

Assembly Process

First, the permeable membrane and the seal are inserted into the lower support 410 through the first opening 411a of the top 411 of the lower support 410 and are placed on the top face of the bottom support portion 415.

The cylindrical lower member 421 of the upper support 420 is inserted into the lower support 410 through the first opening 411a of the top 411 of the lower support 410. In this connection, while the top of the projection 4523 of each hook 452 contacts the edge of the bottom of the cylindrical lower member 421, the edge of the bottom of the cylindrical lower member 421 presses against the top of the projection 4523 via the pressing force to allow the cylindrical lower member 421 to be inserted into the lower support 410. Thus, the vertical extension 4521 and the projection 4523 of each hook 452 are displaced outwardly in a direction away from the outer wall of the cylindrical lower member 421. Then, the opening of the cylindrical lower member 421 reaches the permeable membrane or the seal. In this connection, each hook 452 is displaced inwardly in an elastic manner and thus is fastened to each groove 451 of the cylindrical lower member 421 as shown in FIG. 13.

Thus, the upper support 420 and the lower support 410 are fastened to each other such that the permeable membrane and the seal are sandwiched between the top face of the bottom support portion 415 of the lower support 410 and the opening of the cylindrical lower member 421 of the upper support 420.

Separation Process

When a user wants to separate the upper support 420 and the lower support 410 from each other, the user presses down the horizontal extensions 4522 of two hooks 452 adjacent to each other or two hooks 452 opposite to each other among the four hooks 452 of the lower support 410. The projections 4523 of the two hooks 452 are separated from the two groove 451 respectively. Subsequently, the horizontal extensions 4522 of the remaining two hooks 452 are pressed down, such that the projections 4523 thereof are separated from the remaining two grooves 451 respectively. In this state, the upper support 420 is pulled upward, such that the upper support 420 is separated from the lower support 410.

In this way, only the permeable membrane is placed on the bottom support portion 415 of the lower support 410. Then, only the permeable membrane is separated from the lower support 410 independently.

When using the permeable membrane support (PMS) with the attachable and detachable permeable membrane according to the present disclosure, the permeable membrane may be safely and independently separated from the PMS. Thus, when culturing cells on the PMS and then separating the cell culture from the PMS, the permeable membrane having the cultured cells thereon may be separated from the PMS in an intact layer form while deforming the permeable membrane. Then, the separated permeable membrane is placed on a stage of a microscope and then the culture sample on the permeable membrane is directly measured using the microscope.

Further, due to the snap-fit coupling structure between the upper support and lower support, easy coupling and separation therebetween may be easy. Thus, the coupling and separation between the upper support and lower support may be achieved simply.

Descriptions of the presented embodiments are provided to enable any person skilled in the art of the present disclosure to use or implement the present disclosure. Various modifications to these embodiments will be apparent to those skilled in the art of the present disclosure, and the general principles defined herein may be applied to other embodiments without departing from the scope of the present disclosure. Thus, the present disclosure is not limited to the embodiments presented herein, but should be interpreted in the broadest scope consistent with the principles and novel features presented herein.

What is claimed is:

1. A permeable membrane support having an attachable and detachable permeable membrane, the permeable membrane support comprising:
    a lower support;
    an upper support partially accommodated into the lower support; and
    a permeable membrane disposed between the lower support and the upper support,
    wherein the lower support has a hollow cylinder shape having an outer diameter smaller than an inner diameter of a plate well such that the lower support is accommodated in the well of the plate,
    wherein the lower support has:
        a top having a first opening;
        a bottom having a second opening;
        an inner wall extending between the top and the bottom, wherein an inner open space is surrounded by the inner wall and communicates with the first and second openings; and
        a bottom support portion extending inwardly from the inner wall at a bottom of the lower support, wherein the second opening is centrally located in the bottom support portion and communicates with the inner space;
    wherein the upper support has:
        a cylindrical lower member fitted into the inner space of the lower support, wherein the cylindrical lower member has a bottom opening defined therein;
        an annular disk supported on a top of the well of the plate; and
        a bridge for connecting the cylindrical lower member and the annular disk with each other,
    wherein one of the upper support and the lower support has one of a hook having a projection and a groove to achieve snap-fit engagement therebetween, while the other of the upper support and the lower support has the other of the hook having the projection and the groove to achieve snap-fit engagement therebetween,
    wherein when the upper support and the lower support are engaged with each other in a snap-fit manner, the permeable membrane is sandwiched between the bottom opening of the cylindrical lower member of the upper support and a top face of the bottom support portion of the lower support.

2. The permeable membrane support of claim 1, wherein the permeable membrane includes a porous thin film, and a seal pattern bonded to the porous thin film.

3. The permeable membrane support of claim 2, wherein the seal pattern includes a circular pattern extending along an outer edge of the porous thin film,
wherein when the upper support and the lower support are engaged with each other in a snap-fit manner, the seal pattern is sandwiched between the bottom opening of the cylindrical lower member of the upper support and the top face of the bottom support portion of the lower support.

4. The permeable membrane support of claim 1, wherein the permeable membrane support further comprises a seal disposed on a top face or a bottom face of the permeable membrane and extending along an outer perimeter of the permeable membrane.

5. The permeable membrane support of claim 1, wherein the lower support includes a cylindrical lower portion and an elliptical upper portion, wherein the first opening is elliptical, and the second opening is circular,
wherein the hook includes two opposing hooks extending inwards respectively from both opposing points of the inner wall in a short-axis direction of a top of the elliptical upper portion,
wherein the groove includes two opposing grooves defined in an outer face of the cylindrical lower member to receive the two hooks therein respectively in a snap-fit manner.

6. The permeable membrane support of claim 1, wherein the hook includes at least two hooks extending upwards from a top face of the lower support, wherein each of the at least two opposing hooks is constructed to be coupled to a top of the cylindrical lower member of the upper support in a snap-fit manner.

7. The permeable membrane support of claim 1, wherein the hook includes at least two hooks, each hook having a horizontal extension extending outwardly horizontally from an outer face of the cylindrical lower member of the upper support and a vertical extension extending downwardly from an outer end of the horizontal extension,
wherein the groove includes at least two grooves defined in an outer face of the lower support to receive the at least two hooks therein respectively in a snap-fit manner.

8. The permeable membrane support of claim 1, wherein the lower support has at least two cut-aways, wherein each cut-away is formed by partially cutting away an upper portion of the lower support around each of at least two hooks, wherein each cut-away has an inverse U shape, wherein each hook extends upwardly from a center of a bottom of each cut-away,
wherein the groove includes at least two grooves defined in an outer face of the cylindrical lower member of the upper support to receive the at least two hooks therein respectively in a snap-fit manner.

* * * * *